United States Patent
Eibofner et al.

(10) Patent No.: US 6,217,329 B1
(45) Date of Patent: Apr. 17, 2001

(54) MAINTENANCE APPARATUS FOR A MEDICAL OR DENTAL HANDPIECE

(75) Inventors: Eugen Eibofner, Biberach; Hans-Dieter Wiek, Hochdorf, both of (DE)

(73) Assignee: Kaltenbach & Voigt GmbH, D-88400 Biberach (DE)

( * ) Notice: Subject to any disclaimer, the term of this patent is extended or adjusted under 35 U.S.C. 154(b) by 0 days.

(21) Appl. No.: 09/533,086

(22) Filed: Mar. 22, 2000

(30) Foreign Application Priority Data

Mar. 26, 1999 (DE) .............................. 199 13 946

(51) Int. Cl.[7] .............................. A61C 19/00; A61L 2/02
(52) U.S. Cl. ...................... 433/104; 422/292; 422/300
(58) Field of Search ................. 433/77, 104; 422/6, 422/292, 295, 300

(56) References Cited

U.S. PATENT DOCUMENTS

| | | | |
|---|---|---|---|
| 4,990,087 | * 2/1991 | De Rocchis et al. | 433/104 |
| 5,057,283 | 10/1991 | Guggenheim et al. | 422/116 |
| 5,165,503 | * 11/1992 | Hoffman | 433/104 |
| 5,348,711 | * 9/1994 | Johnson et al. | 422/292 |
| 5,403,555 | * 4/1995 | Steinhauser | 422/128 |
| 5,556,607 | * 9/1996 | Childers et al. | 422/300 |
| 5,723,090 | * 3/1998 | Beerstecher et al. | 422/26 |

FOREIGN PATENT DOCUMENTS

4235699A1   4/1994   (DE) .
0300945B1   12/1992  (EP) .
0598247B1   9/1999   (EP) .

* cited by examiner

*Primary Examiner*—Ralph A. Lewis
(74) *Attorney, Agent, or Firm*—Fitzpatrick, Cella, Harper & Partner

(57) ABSTRACT

The invention relates to a maintenance apparatus (1) for medical or dental handpieces (17), having a housing (2), which encloses a free maintenance chamber (4) which is accessible by means of a door (5), having a plurality of connection parts (16a, 16b) in the maintenance chamber (4) each for receiving the rearward end of a handpiece (17), having a supply line (18) for a maintenance medium, which branches with supply line branches (18a) to the connection parts (16a, 16b), which branches open out each at a mouth opening (16a1, 16b1) at the associated connection part (16a, 16b), which stands in connection with a drive channel of the connected handpiece (17), having a supply system for supplying the maintenance medium to the connection parts (16a, 16b) and having a control device (51) for control of the supply system, whereby a sensor (S2a to S2d) is associated with each connection part (16a, 16b, 16c), which sensor is activated by means of the handpiece (17) connected with the associated connection part and emits a signal to the control device (51), and whereby the supply system supplies the maintenance medium only to the connection parts (16, 16b, 16c) which are connected with a handpiece (17). For the purpose of ensuring an adequate supply of maintenance medium, the supply system supplies the maintenance medium to the connection parts (16a, 16b, 16c) one after another.

12 Claims, 11 Drawing Sheets

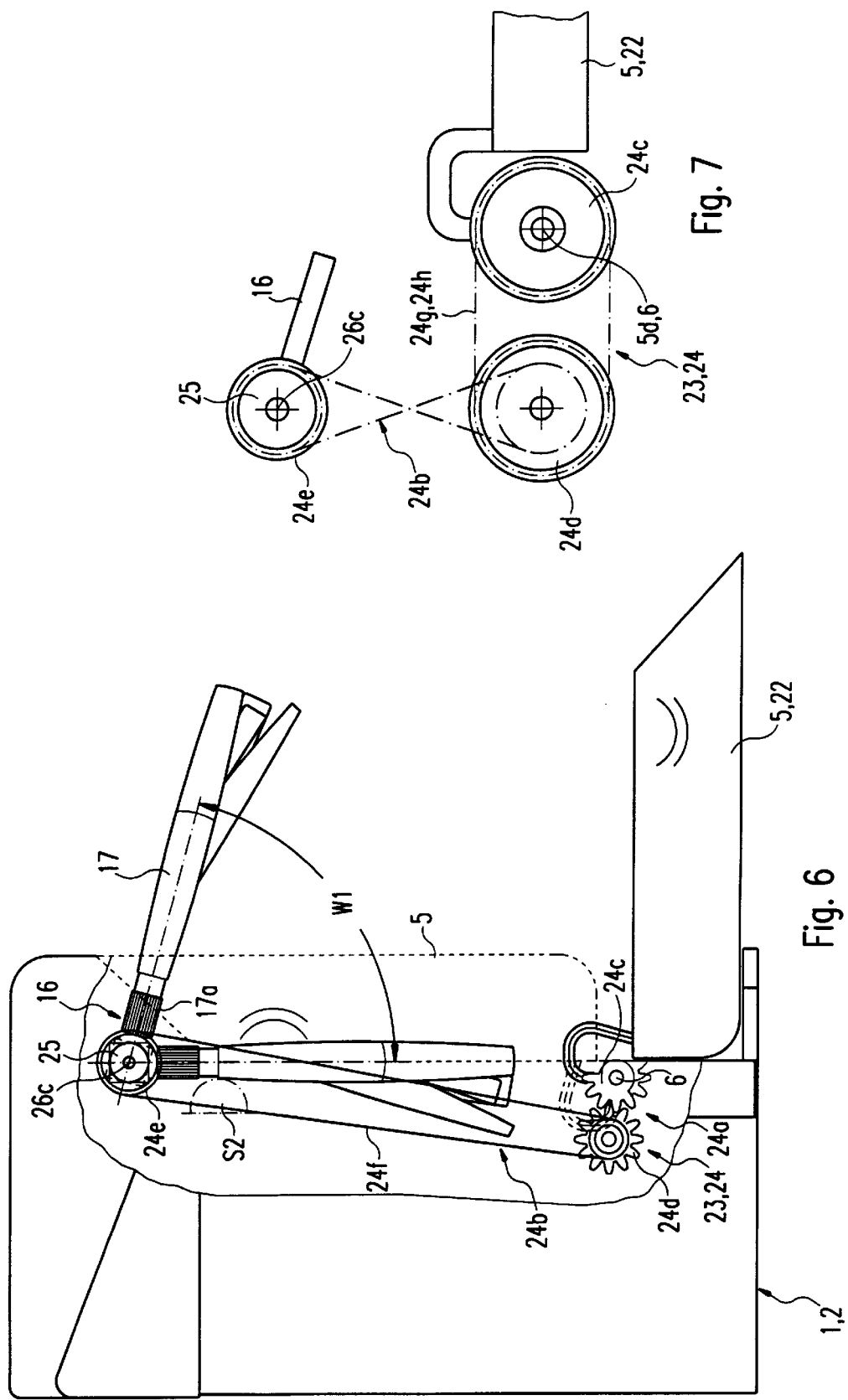

MAINTENANCE APPARATUS FOR A MEDICAL OR DENTAL HANDPIECE

BACKGROUND OF THE INVENTION

1. Field of the Invention

The invention relates to a maintenance apparatus for a medical or dental handpiece, and more particularly it concerns a novel apparatus for selectively supplying a maintenance medium to medical or dental handpieces which are mounted therein.

2. Description of the Related Art

Medical or dental handpieces are tube-like parts, which the doctor grasps during the treatment as grip sleeve. A typical such handpiece is a so-called drill handpiece, which carries the treatment tool at its forward end, e.g. a drill, and can be coupled with its rearward end with a connection part by means of a so-called plug-in/rotatable coupling, through which connection part supply lines for energy for driving the treatment instrument and also fluid lines for treatment media extend, which penetrate the plug-in/rotatable coupling and continue in the handpiece. The fluid lines may be lines carrying air, water or spray, which extend as channels or hose lines up to the forward end of the handpiece and emerge there, directed towards the treatment site. With a so-called turbine handpiece there is provided a compressed air line for supplying the turbine arranged in the forward end region of the handpiece, in a so-called drive channel, which compressed air line likewise penetrates the plug-in/rotatable coupling and extends to the turbine. So-called motor handpieces, which are driven by means of an electric motor, which is arranged in the above-mentioned connection part, likewise have a so-called drive channel, in which a drive shaft section is rotatably mounted, which extends to a spindle carrying the tool, in order to drive this spindle.

In functional operation of the above-mentioned handpieces maintenance is required from time to time, in particular of the drive channel and the drive elements rotatably mounted therein. Here it is to be taken into account that the handpieces, both in the case of motor drive and also turbine drive, may have drive elements rotating at high speed, which in the event of inadequate maintenance are particularly sensitive and rapidly wear, as a result of which repairs are needed.

With a known maintenance apparatus, described in DE 42 35 699 A1, for the maintenance of medical or dental handpieces, there is provided a water bath in which the handpiece is heated and cleaned by means of blowing through cold and/or hot compressed air, and thereafter can be maintained by blowing through a maintenance medium. Several handpieces can be subject to maintenance at the same time, which are held in a hanging or standing arrangement in each case at a connection part on a common carrier, which can be placed from above into a container holding the water bath. With this known maintenance apparatus, the handpieces are manually introduced from above into the container, in a vertical disposition, and connected with the connection parts.

For connecting the carrier with a supply line for a maintenance medium and a supply line for compressed air there is provided a line coupling which is located outside of the container and in the region of which a mechanical non-return valve is so arranged in each of these two lines that upon decoupling the valve body in each case self-actingly closes the fixed parts and line section.

A maintenance apparatus of the kind indicated in the introduction is described in EP 0 300 945 B1. This known maintenance apparatus has a housing enclosing a maintenance chamber which is accessible through a trapdoor having a pivot axis running at its lower edge. A plurality of connection pins for handpieces are provided, which handpieces can be plugged from below onto the connection pins, arranged in the upper region of the receiving chamber. Further, with this known maintenance apparatus, a safety valve is provided which closes the outlet from the connection pin on which no handpiece is placed. For the control of respective through-flows for a water mist and a disinfection mist to the connection parts, a control device is provided with associated electric valves.

With both above-described known maintenance apparatuses the supply of the maintenance medium to the connection parts is effected simultaneously. Here, significant differences between the quantities of maintenance medium supplied can occur between the connection parts, since a flow takes place more where it is subject to the least resistance. Different flow resistances can, however, scarcely be avoided in the region of the supply line branches. Furthermore, in particular different handpieces present the flow of maintenance medium with different flow resistances.

The object of the invention is, with a maintenance apparatus of the kind mentioned in the introduction, to ensure a sufficient supply of maintenance medium for each handpiece or to improve the supply and in particular to make more uniform the supply of maintenance medium.

This object is achieved by means of the structural arrangements described below.

With the maintenance apparatus in accordance with the invention the maintenance medium is supplied to the connection parts one after another, so that the supply to each occupied connection part is effected individually and thus the supplied quantity of maintenance medium can be made on the one hand in a controlled manner and on the other hand with slight quantity differences. With the configuration in accordance with the invention, the maintenance is thus significantly improved and there is effected in particular a reliable maintenance.

The configuration in accordance with the invention is admirably suitable for maintenance medium containers in the form of spray cans which are closed except for their outlet opening and which stand under self-pressure, whereby the issue of the maintenance medium is based on the action of a driver gas, which may be for example butane or isobutane or propane. The configuration in accordance with the invention leads also to a significant simplification, since such spray cans containing maintenance medium are available on the market and thus the maintenance apparatus does not need a special maintenance medium container but rather a conventional spray can, which due to its self-pressure requires no further feed drive for the flow of the maintenance medium. Since the supply capacity of a spray can is restricted due to the driver gas function, the configuration in accordance with the invention is particularly well suited for a spray can, because its capacity is excellently suited for the individual maintenance of the handpieces.

The latter advantages are also achieved by means of the configuration in accordance with the invention according to which the maintenance apparatus has a spray can in combination with such a supply apparatus with which the maintenance medium is supplied at the same time to a reduced number of the connection parts present, preferably in each case two connection parts. In comparison with the maintenance apparatus in accordance with claim 1, with this configuration the maintenance time is reduced.

With both configurations in accordance with the invention, individual steps of the maintenance procedure are automatically controlled, in particular after issue of a start signal, so that the maintenance apparatus works independently and after a maintenance procedure the handpiece or handpieces need only be removed.

The subclaims contain features which improve and intensify the maintenance and also the cleaning of the at least one handpiece and further lead to simple and compact constructions, reliable functioning and longer life time, and which can be economically manufactured.

BRIEF DESCRIPTION OF THE DRAWINGS

Below, the invention and further advantages which can be achieved thereby will be described in more detail with reference to preferred exemplary embodiments. There is shown:

FIG. 6 the device in a side view from the left, partly sectioned for the purpose of illustrating a pivot drive;

FIG. 7 the pivot drive according to FIG. 6, in a modified configuration;

DETAILED DESCRIPTION OF THE PREFERRED EMBODIMENTS

Figure 3:
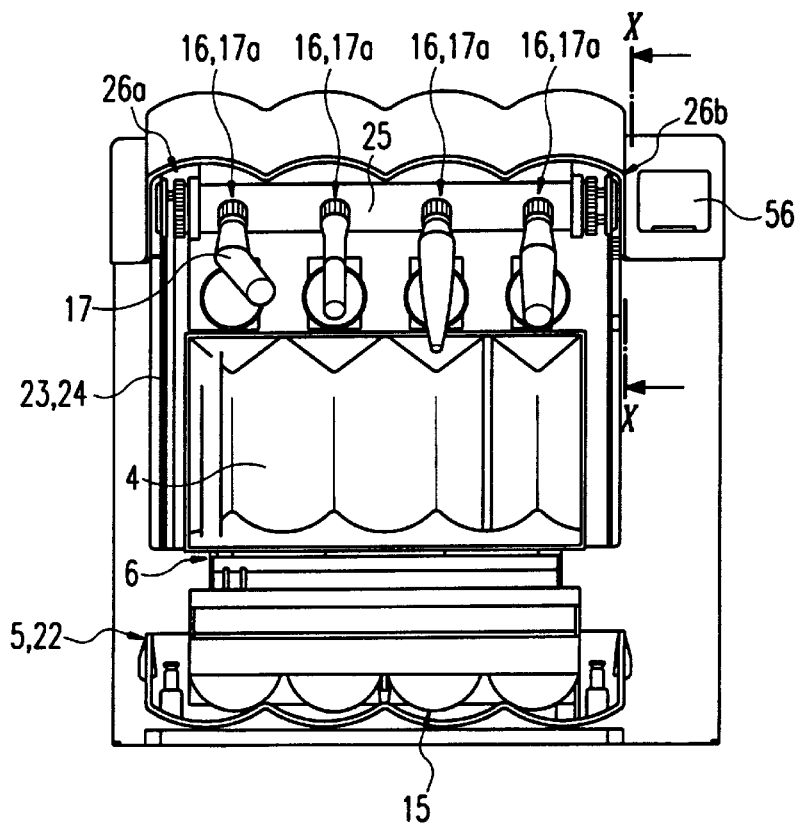
FIG. 3 the device in a view from the front.
Figure 4:
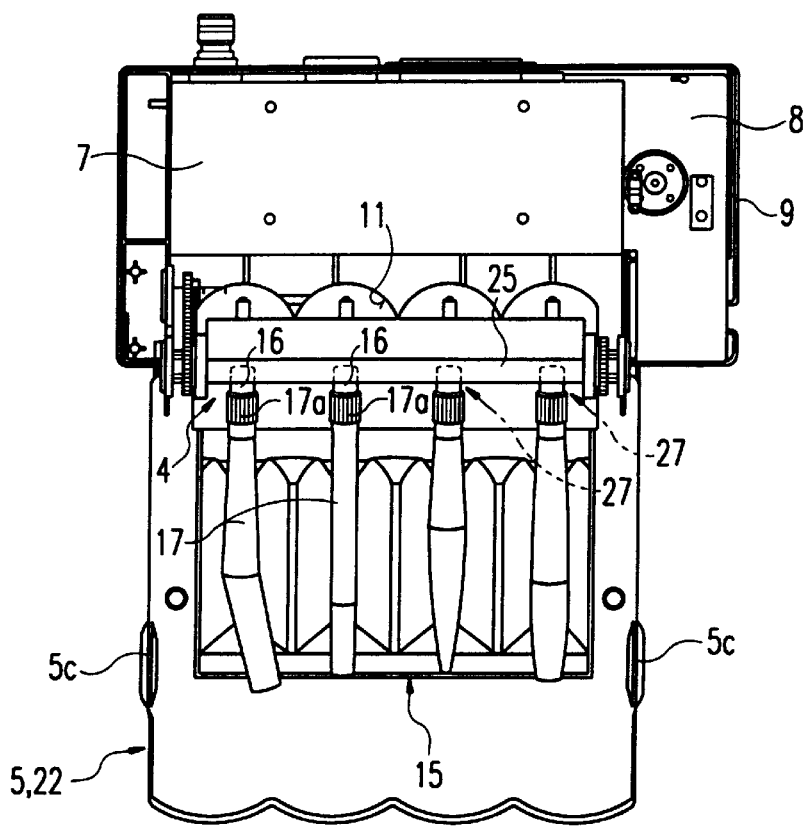
FIG. 4 a device in view from above.
Figure 5:
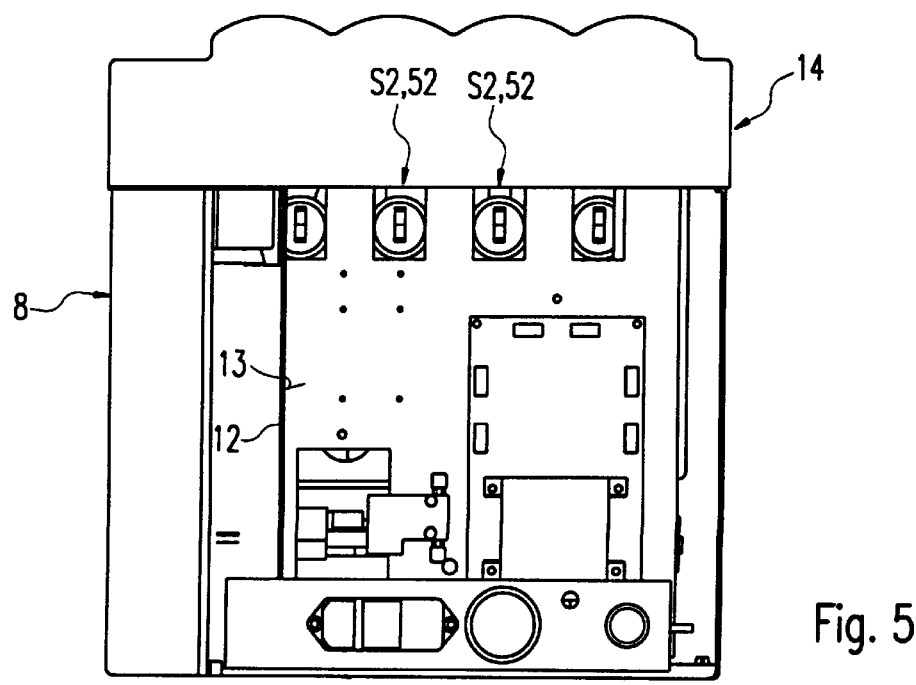
FIG. 5 the device in a view from behind, with opened housing.

As already mentioned, the device includes a compact maintenance apparatus, referenced by 1, the individual parts or components of which are integrated in a housing 2 which in the horizontal cross-section has an elongate, in particular substantially rectangular, cross-sectional form, whereby one broad side forms the forward and operating side 3 at which a maintenance chamber 4 is accessible by means of a door 5 which is selectively opened and closed, in particular a trapdoor which is mounted on the housing 2 pivotably around a pivot axis 6 running horizontally in its lower edge region. The maintenance chamber 4 is located above the pivot axis 6 and is only a forward subchamber of the housing 2, which may have a further rearward subchamber 7 and, if applicable, a further lateral subchamber 8, which in the present configuration is arranged on the right side, whereby the associated side wall is likewise formed by means of a door 9 which can be selectively opened and closed. The forward housing inner chamber 4 is divided by means of an internal wall 11 from the rearward subchamber 7 and divided off by means of an inner side wall 12 arranged between it and the lateral subchamber 8, whereby an inner housing 13 is formed. The inner wall 11 may have a vertically developing wave-like profile, for example with four wave troughs, as FIG. 3 and 4 show. The forward door 5 is preferably formed with a floor wall 5a and two mutually oppositely lying side walls 5b, in a shell or shovel shape. The upper ends of the side walls 5b may be shaped to fall obliquely, in the sense of a bevel angle W, whereby at an upper wall 14 of the housing 2 a correspondingly oblique shape may be present at oppositely arranged upper wall sections 14a. Furthermore, there can loosely placed and form-fittingly positioned in the forward door 5 an inner shell 15, in which—in functional operation—maintenance medium excesses or remnants can collect, which will be described further. The inner shell 15 takes part in the opening and closing movement of the forward door 5. In the region of a wall section of the inner shell 15 which in the opened position forms a rear wall 15a there may be arranged an entry wall 15b—extending rearwardly, e.g. obliquely or rounded, upwardly, the purpose of which will likewise be further described below. Associated with the forward door 5 is a schematically illustrated holder device, e.g. a latching or clamping device, preferably in its upper region, for securing in its—in the present exemplary embodiment, tilted up—closure position. For this purpose there may serve e.g. clamping or latching parts 5c arranged at the edges of the side wall 5b. The upper wall 14 is preferably likewise releasably fixed, in particular by means of a quick-fastening connection, e.g. by means of a latching device, which for reasons of simplification is not illustrated.

In the maintenance chamber 4 there is arranged at least one plug-in coupling or plug-in connection having a plug-in connection part 16 for a mechanical and hydraulic connection for a handpiece 17 to be subject to maintenance in the maintenance apparatus 1, the coupling or connection being arranged in such a position that the handpiece 17—in the plugged-in disposition—is located completely within the inner housing 13 and the maintenance chamber 4 can be closed by means of the forward door 5 partly forming that chamber. The plug-in connection part 16 is preferably arranged in the upper region of the maintenance chamber 4, so that the handpiece 17 can be plugged thereon and positioned in a hanging disposition. Preferably there are arranged a plurality of plug-in connection parts 16, e.g. four, in a row extending parallel to the operating side 3, which plug-in connection parts may have the same or different connection shapes on which respective handpieces 17 of different configurations—which may originate from one and the same or from different manufactures, or which have different functions—can be connected and maintained. The plug-in connection part or parts 16 are each compatible with a plug-in coupling part 17a arranged at the rearward end of the associated handpiece 17. With the present configuration, the plug-in connection parts 16 are formed by plug-in pins, onto which the handpieces 16 can be plugged in each case with a suitable plug-in recess. The plug-in connection part or parts 16 are connected with a maintenance medium supply line 18 which extends from a connection device 19 for a source of maintenance medium, in particular a maintenance medium supply container 21.

The plug-in connection part or parts 16 are, if appropriate, mounted pivotably, e.g. around an angle W1 of about 45° to 90°, between a functional disposition, in which the handpiece or handpieces 17 are located completely within the maintenance chamber 4, and an operating disposition in which they project out of the opened maintenance chamber 4, and thus can be readily connected or removed. With the present configuration, the plug-in connection parts 16 are directed downwardly in their functional disposition, whilst they are directed towards the operating side 3 in their coupling or operating disposition, e.g. being horizontally or obliquely downwardly directed. Thereby it is advantageous to provide a pivot mechanism 23, accessible from the outside, with regard to the housing, by means of an actuating member 22, with which mechanism the plug-in connection part or parts 16 can be pivoted. With the present exemplary embodiment, the actuating member 22 is formed by means of the forward door 5, which by means of a drive connection 24 is so connected with the plug-in connection part or parts 16a that upon opening of the forward door 5 they are self-actingly pivoted into their operating disposition, and upon closing are self-actingly pivoted into their functional disposition. With the present configuration, there is provided a common carrier 25 for the plug-in connection parts 16, in the form of a horizontally extending rod or pivot shaft, which is pivotally mounted to both sides of the maintenance chamber 4, at the side walls of the inner housing 13, in associated pivot bearings 26a, 26b.

Preferably, the respective plug-in connection part or parts 16 are releasably connected with the associated carrier 25 by means of a connection device, whereby the connection devices for all plug-in connection parts 16 are similar. By these means it is possible to exchange the plug-in connection part or parts 16 for a plug-in connection part of different shape and/or size, whereby the maintenance apparatus 1 can be adapted to handpieces 17 of different shape, configuration and size, e.g. to handpieces 17 of different manufacturers. The connection device, designated with 27, may be a pin connection having a securing element, e.g. a securing screw, for securing the plug-in pin—preferably arranged on the plug-in connection part 16—in a suitable position preferably in a plug-in recess arranged in the carrier 25, in the plugged together disposition.

Since the forward door 5 and the carrier 25 of the at least one plug-in connection part 16 carry out mutually opposing pivot movements, there is needed a drive connection 24 which reverses the movement, in this case the pivot movement. With the exemplary embodiment according to FIG. 6, the drive connection 24 is formed by means of a combined gear wheel drive 24a and belt drive 24b, in particular toothed belt drive. Thereby there is arranged a wheel 24c, having teeth, on a pivot shaft 5d of the forward door joint, which engages with a second wheel 24d, likewise having teeth, which is mounted in parallel pivotably in the housing 2, preferably behind the wheel 24c. The second wheel 24d stands in drive connection with a belt disk 24e—arranged on the carrier 25 of the plug-in connection part or parts 16, here on the pivot shaft—by means of a belt 24f, in particular a toothed belt.

As FIG. 7 shows, there may also be provided between the wheels 24c, 24d a belt drive 24b having a belt 24h, whereby the belt drive 24b is arranged with belt runs which cross over, by which means the necessary reversal of direction of movement is attained.

Figure 8:
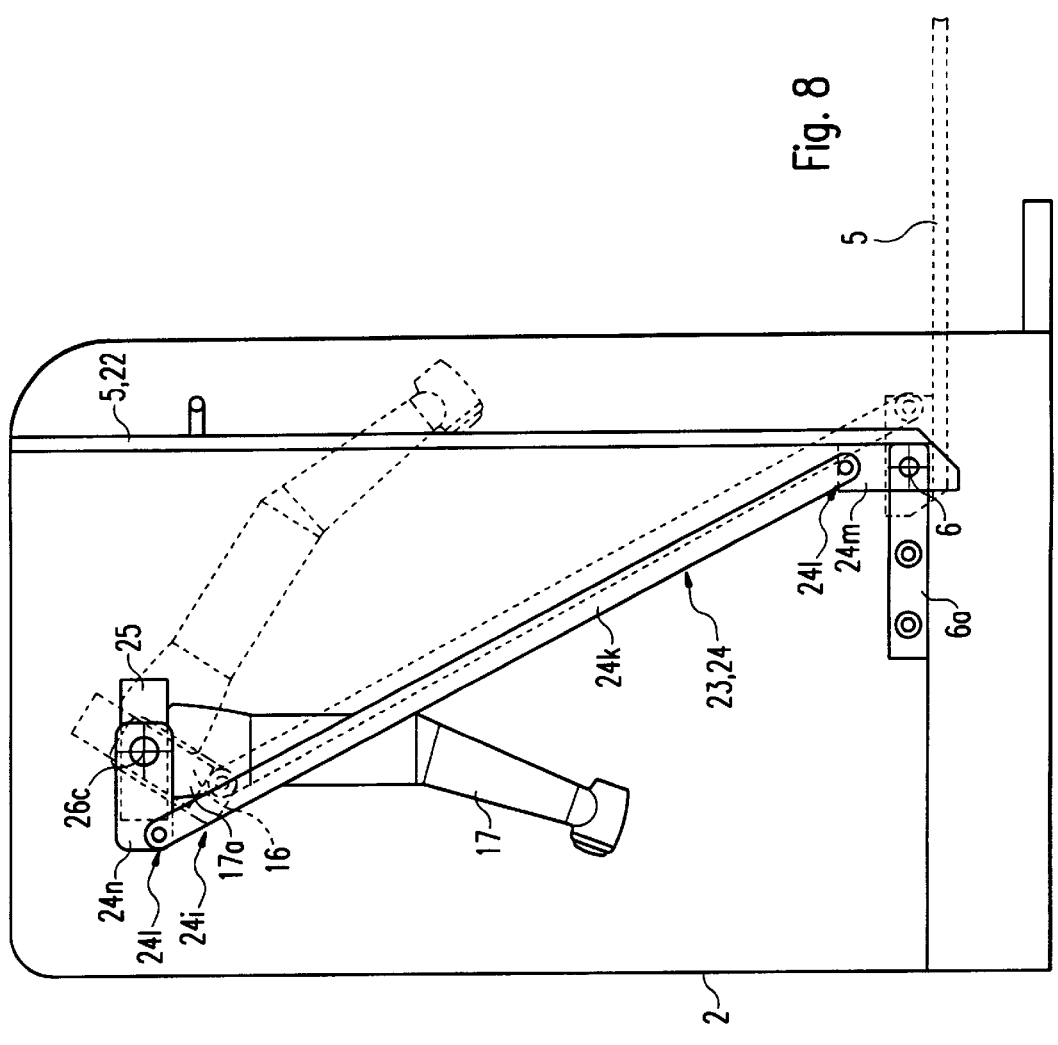
FIG. 8 the device in a side view from the left, with a pivot drive in a further modified configuration.

With the exemplary embodiment in accordance. with FIG. 8, in which the same or similar parts are likewise provided with the same reference signs, the drive connection 24 is formed by means of a lever drive 24i having a lever 24k, which is connection with lever arms 24m, 24n in each case by means of a joint 24l, of which lever arms the lever arm 24m is pivotable around the pivot axis 6 and connected with the forward door 5, whilst the lever arm 24n is pivotable around the pivot axis 26c of the pivot bearing 26a, 26b and is connected with, or forms, the plug-in connection part or parts 16, or the carrier 25 thereof. In the case that a plurality of plug-in connection parts 16 are pivotable in common, only one drive connection 24 is needed which is preferably arranged in the vicinity of a lateral edge region of the forward door mounting. With the configuration according to FIG. 8, a bearing part 6a of the pivot bearing for the forward door 5 is provided as a screw part which is screwed onto an associated housing wall, e.g. onto the inner housing 13. With the exemplary embodiment according to FIG. 8, the pivot axis 26c is, with regard to the arrangements in the other exemplary embodiments, arranged more inwardly set back in the housing 2. The illustrated and described lever drive 24i is suitable also for an arrangement of the pivot axes 6, 26c in which these are arranged in substance above one another, such as FIG. 6 for example shows.

With the present exemplary embodiment, the maintenance medium supply container 21 is provided as maintenance medium source, which can be readily and rapidly connected with the housing 2 and with the maintenance medium supply line 18, and readily and rapidly exchanged, by means of a quick coupling or quick-fastening connection 29, in which there are preferably integrated a mechanical quick-fastening connection 31 and a flow-related or hydraulic quick-fastening connection 32. The mechanical quick-fastening connection 31 has a quick-fastening connection part 31a associated with the housing 2 and a quick-fastening connection part 31b associated with the supply container 21. The former is constituted by means of a plug-fitting having a plug recess 31c into which the supply container 21 can be plugged preferably from below, and is securable by means of a securing element. The securing element is preferably an elastically yielding element or a securing element formed by means of a magnetic coupling 33, whereby the elastic yieldability or releasability is so dimensioned that upon release of the supply container 21 the securing element can be manually overcome with a small application of force.

With the present configuration, the supply container 21 is a spray can, and the maintenance medium is a fluid, in particular a maintenance oil, which, in conventional manner, stands under self-pressure in the spray can due to a gaseous drive medium, in particular propane or butane, likewise contained in the spray can, and upon opening of a blocking valve V1, preferably formed as a non-return valve, below the outlet opening 34 of the spray can, self-actingly exits from the spray can and arrives in the supply line 18 by means of the hydraulic quick-fastening connection 32.

The supply container 21, of steel, in particular of tin plate, has the outlet opening 34 in a dome-shaped cover section 35 which starts from an upper peripheral edge 36 of the supply container 21. The plug-fitting has preferably an in particular oblique or hollow conical shaped guide surface 37, to which there adjoins upwardly the plug-in recess 31c with an annular shoulder surface 38 forming its base, whereby upon plugging into the plug recess 31c the supply container 21 finds a ready centering and a stop, and an abutment on the annular shoulder surface 38 with a second peripheral edge 36a, which is arranged in the base region of the dome shape.

In this disposition, the cover section 35—in the present exemplary embodiment dome-shaped—and the outlet opening 34—with the blocking valve V1 contained therein—penetrates the annular shoulder surface 38, whereby the blocking valve V1 is pushed open by a sleeve-shaped opening pin 39 which projects downwardly from an upper wall 31*d* of a cap-shaped holder part 40 having the plug-in recess 31*c*. In the pushed open condition, the end faces of the sleeve-shaped opening pin 39 and the closure part of the blocking valve V1*a*, directed towards one another, bear against one another under an elastic spring tension, whereby the thus formed passage for the fluid or spray flow, extending through the opening pin 39, is sealed. The holder part 40 forms an apparatus part 40*a* which due to the coupling attraction force, in the case of an approach movement beyond a minimum spacing, attracts the container 21 in the sense of a snap connection and draws the container 21 into the coupling or plug-in connection. For release, the coupling force can be overcome by means of a certain pulling force and the container 21 thus released.

In the case of the presence of a magnetic coupling 33 the annular shoulder surface 38 is arranged on a permanent magnet part, which may be a ring magnet or a keeper ring 41. The keeper ring 41 may stand in magnetic connection with a magnet ring 42 preferably arranged thereunder, which preferably bears directly thereon and can form the peripheral wall of the plug-in recess 41*c*. For increasing the magnetic force there is preferably provided a second keeper ring 43 which may bear on the magnetic ring 42 from below, and cooperates with a peripheral edge surface 44—here conical shaped—arranged on the peripheral wall of the supply container 21, spaced axially downwardly from the peripheral edge 36*a*. The magnet part having the ring shoulder surface 38, in this case the keeper ring 41, or the above-described magnet arrangement, are arranged in a holder part 40 of non-conductive material, e.g. plastics. With the present configuration the opening pin 39 is arranged on a pin holder 45 which forms the base wall of the holder part 40, preferably formed with a pot shape, and which carries e.g. screwed in, a blocking valve V2 likewise formed by means of a non-return valve, preferably on the upper side. The blocking valve V2 closes in the opposite closure direction to the blocking valve V1 and has a preferably ball or conical shaped valve body which in the through-channel present—due to its own weight or the tension of a spring (not shown) self-actingly closes the through-channel against the flow direction indicated with the arrow 48, and self-actingly opens under flow pressure. There may be arranged on the blocking valve housing 46 a connection port 47 for the connection of a continuing supply line 18, e.g. in the shape of a hose.

Figure 1:
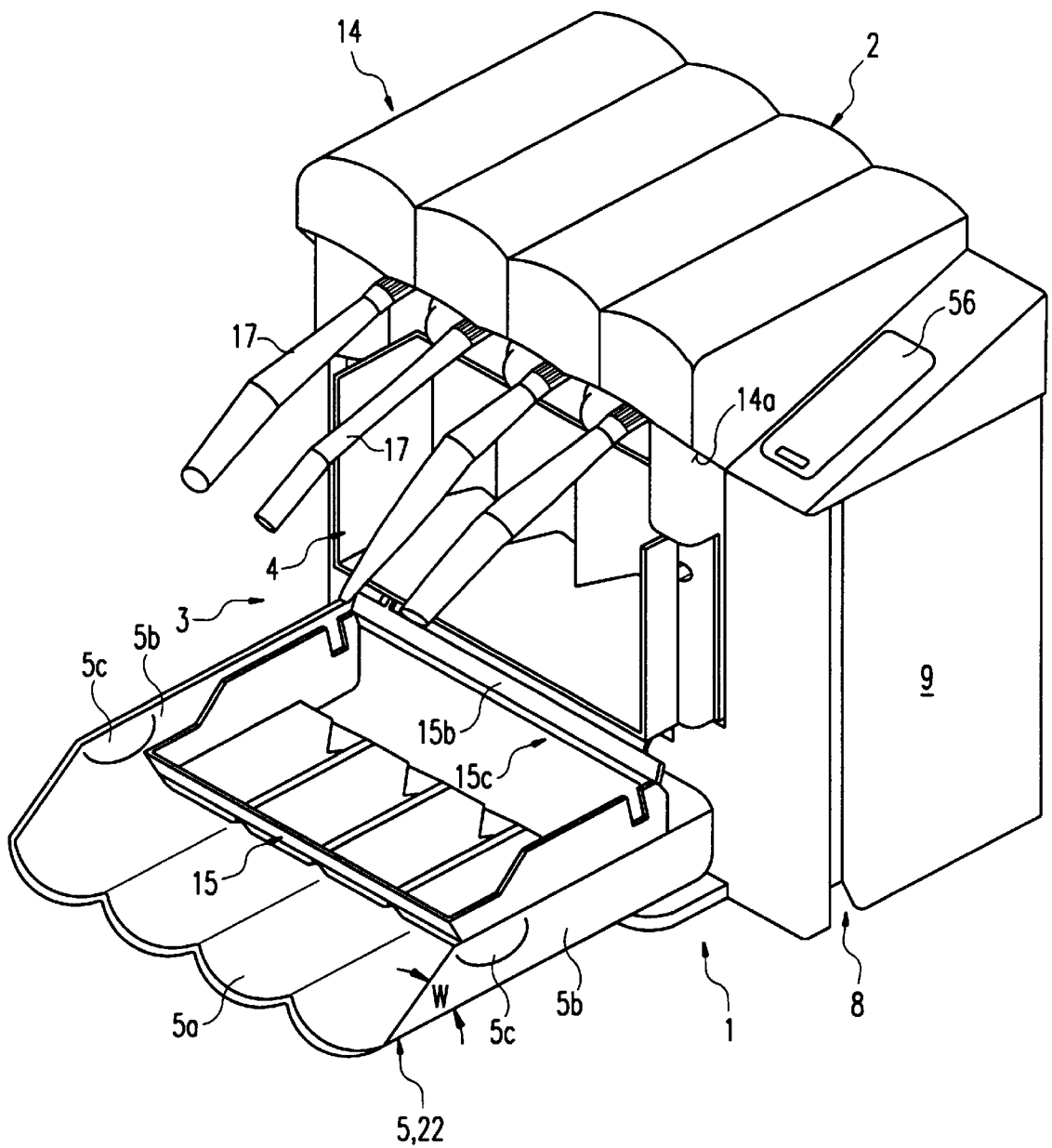
FIG. 1 a device for the maintenance of medical or dental handpieces, in the form of a compact maintenance apparatus having a housing which is in its open condition, in a perspective view from the front.
Figure 2:
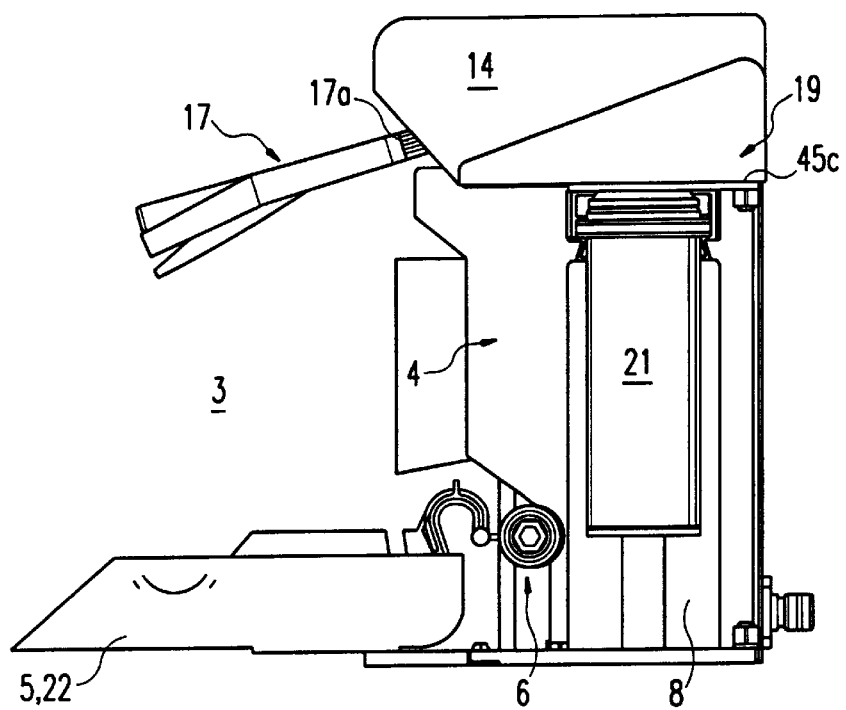
FIG. 2 the device in a side view from the right.

As FIGS. 1 and 3 in particular show, the connection device 19 for the supply container 21 is located in the upper region of the lateral subchamber 8 at a vertical spacing from the base wall of the housing 2, which is larger by a sufficient amount than the height of the supply container 21, such that with open side door 9 the supply container can be manually placed in the lateral subchamber 8 and then upwardly plugged into the plug-in fitting, whereby the first blocking valve V1 is self-actingly opened. The holder part 40 may be attached to a particular inner upper wall 45*c*, or may constitute this wall.

In the supply line 18 behind the blocking valve V2, in the direction of flow, there is arranged a third blocking valve V3 which can be selectively opened and closed by means of an associated mechanical control line 49 by means of an electronic control device 51 (FIG. 12) present—see the illustrated 2/2-way valve. Further, there is arranged in the supply line 18, in the direction of flow, preferably behind the blocking valve V3, a sensor S1, in particular in the form of a light barrier, for determining whether maintenance medium is present in the supply line 18 or not. By these means it can be determined whether the supply container 21 still contains a reserve or is already empty. When the sensor S1 is formed by means of a light barrier, it is advantageous to form the supply line 18 in the region of the light barrier, or overall, of transparent material, e.g. glass or plastics. The third blocking valve S3 and the sensor S1 are, in the case of the presence of a plurality of plug-in connection parts 16, arranged in the supply line before this line branches to the plug-in connection parts 16*a*.

In particular when a plurality of plug-in connection parts 16 are present, there is present in the region of the or each position with a handpiece 17, formed by means of the associated plug-in connection parts 16, a second sensor S2 which determines whether a handpiece 17 is located at the respective plug-in connection part 16. In the present configuration, the sensor S2 is formed in each case by means of an electrical switch 52 which may be actuated directly or indirectly by means of the associated handpiece 17 or plug-in connection part 16. Preferably there is associated with each switch 52, in particular when a microswitch is concerned, a so-called lost motion connection 53, which even after the actuation of the switch 52 makes possible a further movement of the part effecting the switching action, in this case of the associated plug-in connection part 16 or handpiece 17, whereby this movement is taken up by the lost motion switch element 53*a*, without it being further delivered to the switch 52, e.g. in that the switch element 53*a* is elastically compressible.

Figure 9:
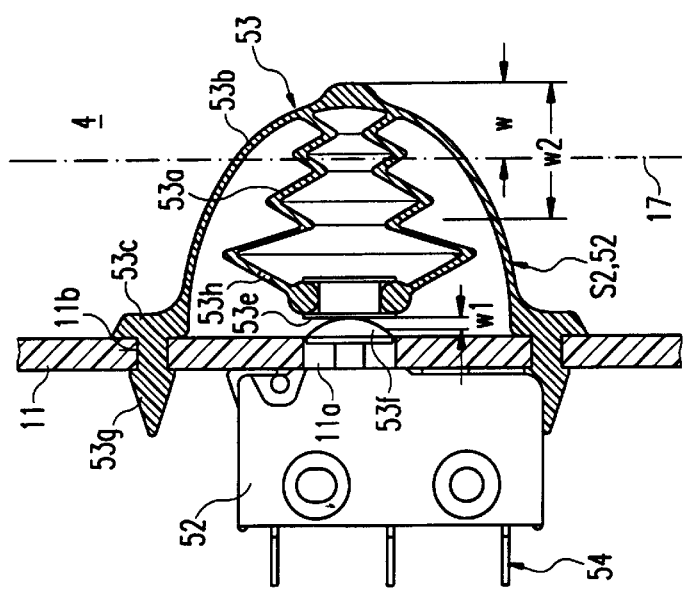
FIG. 9 a switch of the device, in section.
Figures 10, 11:
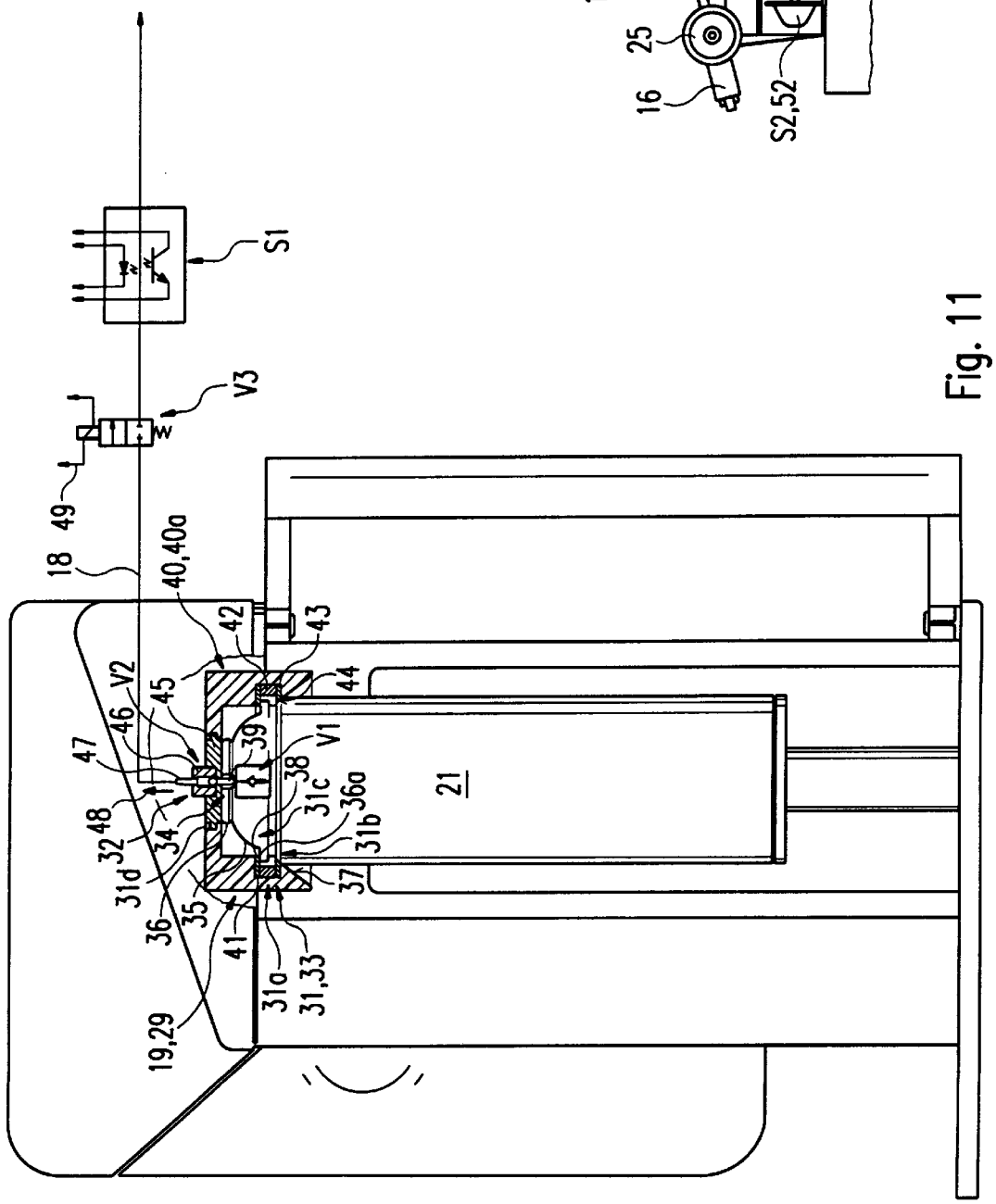
FIG. 10 the partial section X—X of FIG. 3.
FIG. 11 the device in a side view from the right, with opened housing.

With the present configuration, the switch 52, preferably with the lost motion connection 53, is in each case so arranged in the region of the associated plug-in connection part 16 that the switch is actuable by the rearward end region of the associated handpiece 17. Thereby, the arrangement is so made that the handpiece 17 having the smallest cross-sectional dimension is capable of actuating the lost motion connection 53 and the switch 52. Thereby, a handpiece of greater cross-sectional dimension can also be used, since in this case the greater movements of this handpiece upon pivoting into the functional disposition are taken up by the lost motion connection 53, without the switch 52 being damaged. The switch or switches 52 can in each case be arranged on the inner wall 11 extending with a wave form or linearly. With the exemplary embodiment according to FIG. 9 the switching element 53*a*, elastically compressible in the longitudinal direction of the spacing between the switch 52 and the handpiece 17, is arranged on a pot-shaped housing wall 53*b*, which with the present exemplary embodiment is shaped in the sense of a U-shaped or approximately hemispherical shaped bellows, and bears with its edge 53*c* on the housing inner wall 11 and can form a ring seal. The edge 53*c* may have the form of a flange. In the middle contact disposition with the middle handpiece 17, the housing wall 53*b* may have on the outside an e.g. button-like thickening 53*d*. The switch element 53*a*, preferably arranged inwardly on the housing wall 53*b* and in particular connected therewith in one piece, has in the present exemplary embodiment the shape of a bellows the end edge of which towards the wall 11 may be arranged directly or indirectly, by means of a central compression member 53*e* attached to the end edge, in the neutral position, directly neighbouring or on a plunger 53*f* of the switch 52, which may be e.g. a microswitch. The housing wall 53*b* forms a seal closed in itself for the switching element arranged therein. With the present configuration, the switch 52 is arranged on the side of the wall 11 away from the switch element 53a, whereby its switch plunger 53f penetrates a hole 11a in the wall 11, with play for movement. The housing wall 53b is connected with the wall 11, preferably releasably connected, by means of a quick-fastening connection, e.g. in the form of a plug-in connection or latch connection. With the present exemplary embodiment, there are formed on the edge 53c, distributed around the periphery, a plurality of arrow shaped head pins 53g of elastic material, which can be plugged through associated holes 11b in the wall 11 and latch therebehind. The elastic material of the lost motion molded part, described so far and preferably molded in one piece, may be e.g. rubber or plastics. There is preferably present in the bellows a ventilation opening 53h.

The arrangement or size of the molded part is such that the associated handpiece 17, in its functional disposition, presses the molded part together by an amount w, whereby the switch 52 is contacted and issues a signal by means of an associated control line 54 to the control device 51, which corresponds to the functional state "handpiece 17 present". With a handpiece 17 which is smaller in cross-section, the path w is correspondingly smaller, and greater with a handpiece greater in cross-section, whereby a lost motion path w2 is available. A movement of the handpiece 17 extending into the range of the lost motion path w2, upon pivoting in, does not affect the switch 52. Upon a removal of the handpiece, the molded part springs back self-actingly to its initial shape illustrated in FIG. 9, due to its elasticity, whereby the switch 52 is released.

Figure 12:
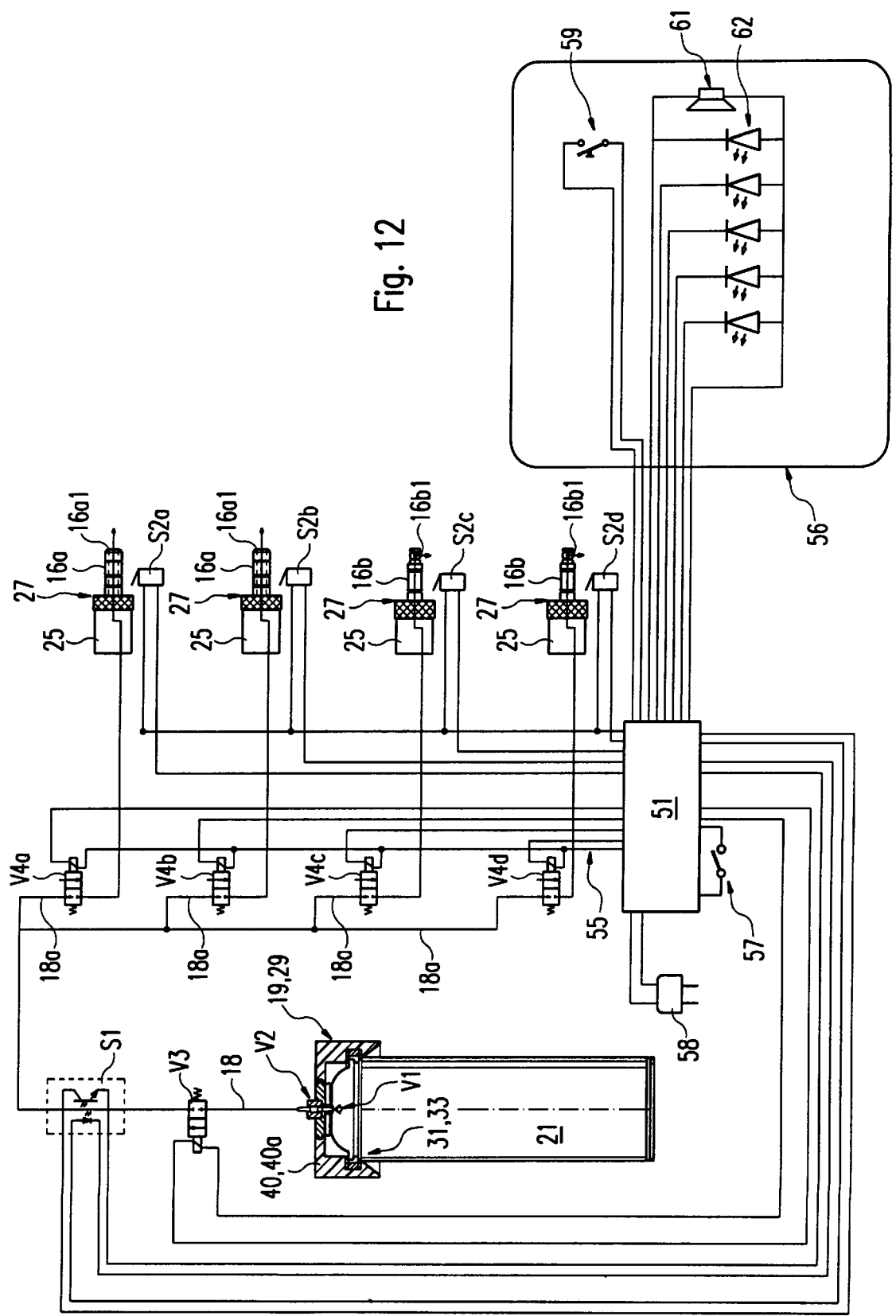
FIG. 12 a circuit diagram for a first exemplary embodiment.

As the circuit diagram according to FIG. 12 and following Figures show, there is associated with each sensor S2a to S2d a fourth blocking valve of the blocking valves V4a to V4d, in an associated supply line branch 18a, which branches from the supply line 18 and extends through the carrier 25 to the associated plug-in connection part 16. When any plug-in connection part 16 is not occupied by a handpiece 17, this non-occupied state is detected by the associated sensor S2a to S2d. In response to a corresponding signal, the associated blocking valve V2a, V2d is controlled by the control device 51 and closed, in order to avoid the issue of maintenance medium at the associated plug-in connection part 16. The control of the blocking valves V4, preferably formed as electro-magnetic valves, is effected by means of electrical control lines 55.

As already mentioned, there are handpieces 17 of different configurations, in terms of shape, size and function, which on the one hand result from different manufacturers and on the other hand from different functions. Handpieces 17 of different functions are in particular handpieces for an electric motor drive, which is located in a so-called connection part having a connection pin corresponding in substance to the plug-in connection part 16, onto which the associated handpiece 17 can be plugged, whereby upon plugging-in a drive shaft arranged in the handpiece 17 is brought into mechanical coupling connection with a drive shaft section arranged in the coupling pin. Such a handpiece has a so-called drive channel, running longitudinally approximately in the middle, in which a drive shaft train is rotatably mounted, which from time to time is to be cleaned and subject to maintenance, which is effected with the present maintenance apparatus 1. Further, such a handpiece 17 has one or more media channels for e.g. air, water or spray, which extend longitudinally through the handpiece 17, off center, and so emerge at its forward end that the stream of medium is directed at the treatment site, in order e.g. to blow this site free, to rinse it or to cool it. These media channels begin in the region of the plug-in recess of the handpiece 17, whereby upon coupling of the handpiece 17 to an above-mentioned connection part they are brought into connection with a corresponding number of media lines which open out at the outer surface of the coupling pin in the region of a ring groove in the outer surface of the coupling pin, sealed to both sides, and/or in the inner surface of the plug-in recess of the handpiece 17. By this means, in the coupled state, media passage through the plug-in coupling present between the connection part and the handpiece 17 is ensured in all relative rotational positions of the handpiece 17. The above-described configurations are known per se and therefore do not need to be described in further detail.

The other main kind of handpiece 17 is a so-called "turbine", namely a handpiece 17 having a turbine drive, arranged in the forward end region, for the tool. The turbine drive is driven by means of a compressed air flow, which is supplied through an air line which extends, using the same principle as the above-described media lines, through the plug-in coupling present between a connection part and such a handpiece 17, up to the turbine drive, which is also likewise known per se.

In order to be able to subject such different handpieces 17 to maintenance, different plug-in connection parts 16 are provided which are compatible with associated handpieces 17. With the present configuration, there are provided two plug-in connection parts 16a for so-called motor handpieces and two plug-in connection parts 16b for so-called turbine handpieces, so that in each case two motor handpieces 17 and two turbine handpieces 17 can be subject to maintenance of the same time.

With the configuration in accordance with FIG. 12, the maintenance apparatus 1 is so formed that only the so-called drive channel in the handpiece 17 is subject to maintenance, which will be described below. For this purpose, the plug-in connection parts 16a have an axial channel opening 16a1 which with a plugged-in handpiece 17 stands in connection with the associated drive channel. In contrast, the plug-in connection parts 16b have, e.g. in their forward end region, a radial exit opening 16b1, which with a plugged-in handpiece 17 in each case stands in connection with the above-described compressed air channel of the associated handpiece 17, extending to the turbine drive, which is a so-called drive channel.

With the maintenance apparatus 1 there is provided for its control a key field 56 having keys or key surfaces, which for reasons of simplification are not shown individually. An advantageous position for arrangement of this key field 56 is the upper side of the housing 2 or lid e.g. in the side end region, and preferably in a position inclined with respect to the operating side 3. Further, there is provided an electrical door switch 57 for the forward door 5, which when the forward door 5 is closed issues a signal to the control device 51 through a control line.

In the following, the function of the maintenance apparatus 1 in the configuration according to FIG. 12 and a working procedure for its operation, will be described.

To prepare the maintenance apparatus 1 for a maintenance procedure, a mains plug 58 is to be connected to an electrical supply mains, the supply container 21 for the maintenance medium is to be connected to the connection device 19, at least one or more handpieces 17 are to be coupled, with open forward door 5, to associated plug-in connection parts 16—here to be plugged on—and the forward door 5 is to be closed, whereby simultaneously the handpieces are self-actingly pivoted into their maintenance disposition. Insofar as there is to be subject to maintenance a handpiece 17 which does not match any of the plug-in connection parts 16 present, then a suitable plug-in connection part 16 can be readily and rapidly mounted or exchanged with the aid of the plug-in connection device 27. Plug-in connection parts 16 suitable for conventional handpieces 17 belong as a component set to the maintenance apparatus, or they can at least be ordered, whereby they then likewise belong to the maintenance apparatus 1 and are available.

Upon closure of the forward door 5, the plug-in connection parts 16 with the plugged-on handpieces 17 pivot into their approximately upright maintenance disposition, whereby they actuate the associated sensors S2. The sensor or sensors S2a to S2d send a signal to the control device 51 which determines which plug-in connection part or parts 16 are occupied with handpieces 17 or not. In correspondence to the signals, in the further maintenance procedure, the associated blocking valves V4a to V4d are opened so that the maintenance medium can flow to the associated plug-in connection part 16 and handpiece 17.

The operating person now starts the maintenance procedure with a manual actuation of a start key 59, whereafter the maintenance procedure runs automatically controlled by means of the control device 51.

Upon connection of the supply container 21, the first blocking valve V1 was already self-actingly opened. The second blocking valve V2 opens self-actingly under the pressure of the maintenance medium. After starting, the valve V3 is opened by means of the control device 51. At the same time, or directly afterwards, the first distribution valve V4a is also opened. The sensor S1 determines whether maintenance medium is flowing in the supply line 18 or not. In the present exemplary embodiment there is exploited for this purpose the fact that the maintenance medium, after leaving the supply container 21 and the expansion thereby taking place, foams up, which is registered by the sensor S1, e.g. formed by means of a light barrier. If maintenance medium is recognized in the supply line, the actual maintenance procedures of the handpieces 17 are carried out one after another. Otherwise, i.e. when no maintenance medium is detected, the control device 51 switches the maintenance device 1 to fault, in response to the signal of the sensor S1.

The control device 51 recognizes, from the supplied signals of the sensors S2a to S2d, which plug-in connection parts 16 are occupied with a handpiece 17. These plug-in connection parts 16 are supplied with maintenance medium one after another in a particular sequence. During this maintenance, in each case a particular quantity of maintenance medium is conveyed through the drive channel of the handpiece 17, which cleans, lubricates and conserves the drive shaft parts rotatably mounted in the drive channel. After a certain opening time, the control device 51 switches the distributor valve V4a to V4d concerned off. Upon switching off of the last distribution valve V4a to V4d the main valve V3 is closed, simultaneously order somewhat previously, e.g. 0.5 seconds previously.

Due to the flow effect, the maintenance medium also has a cleaning effect, with which the drive channel is cleaned, e.g. of old lubrication medium remnants. This flow and cleaning effect is increased in that the maintenance medium, upon emergence from the supply container 21, due to the expansion and the effect of the drive gas, foams and thereby multiplies its volume. By means of this increase in volume, the through-flow and the cleaning effect is promoted. Further, it is advantageous to use a maintenance medium which contains a solvent which is preferably unsaturated and upon throughflow dissolves and carries away old maintenance medium components. The maintenance medium flowing through the handpiece 17 runs out at the forward end of the handpiece 17, whereby it is collected in a receiving trough 15c of the upstanding door 5. In the pivoted-out, open disposition of the door 5, drips of maintenance medium are likewise directed into the receiving trough 15, 15b by means of the guide slope 15b.

When all occupied plug-in connection parts 16 have been supplied with maintenance medium, an acoustic signal, e.g. an alarm buzzer 61, sounds for a short time, e.g. about 2 seconds. At the same time LEDs 62 light up, which belong to the plug-in connection parts 16. These can e.g. be illuminated for so long until the plug-in connection parts 16 are no longer occupied.

The quantity of maintenance medium and the maintenance time for each handpiece 17 is preferably variable, which may be effected continuously or in steps. The control device 51 is configured for this purpose and manually actuable. The maintenance time may be e.g. 0.5 to 2 seconds, and be increasable or reducible in steps of e.g. 0.5 seconds, or be continuously increasable or reducible.

Should a fault appear, in the form of "no maintenance medium present" (sensor S1), the control device switches the maintenance procedure off. So that this is recognized by the operator, associated or all LEDs 62 on the operating field flash. A symbol "change container" also illuminates. After exchanging of the container 21, or of the spray can, the commenced maintenance procedure must be started anew. The apparatus behaves in the same manner if, during the maintenance, a handpiece 17 falls from the plug-in connection parts 16. The electronics recognizes this event by means of the now missing signal of the associated sensor S2a to S2d. As a signal, all LEDs 62 again flash, with the exception of that which indicates the spray can exchange.

As further monitoring function, whether the door 5 is closed or not, sensor S2a to S2d can likewise be employed. only when at least one sensor S2a to S2d sends a signal to the electronics, is the door 5 also closed. In other cases, that is when no signal comes from a sensor S2a to S2d, start of the maintenance procedure does not take place. Thereby, two conditions can be checked. First: plug-in connection part 16 occupied and door 5 open, results in no signal from the associated sensor S2a to S2d, actuate start button, results in no maintenance procedure. Second: no plug-in connection part 16 occupied, no signal from sensor S2a to S2d, start button actuated, results in no maintenance procedure.

Within the scope of the invention it is possible to supply all occupied plug-in connection parts 16 simultaneously with maintenance medium, i.e. to simultaneously open the distributor valves V4a to V4d. This, however, would exceed the capacity of the spray can, which distinguishes itself by simple handling and functioning.

Figure 13:
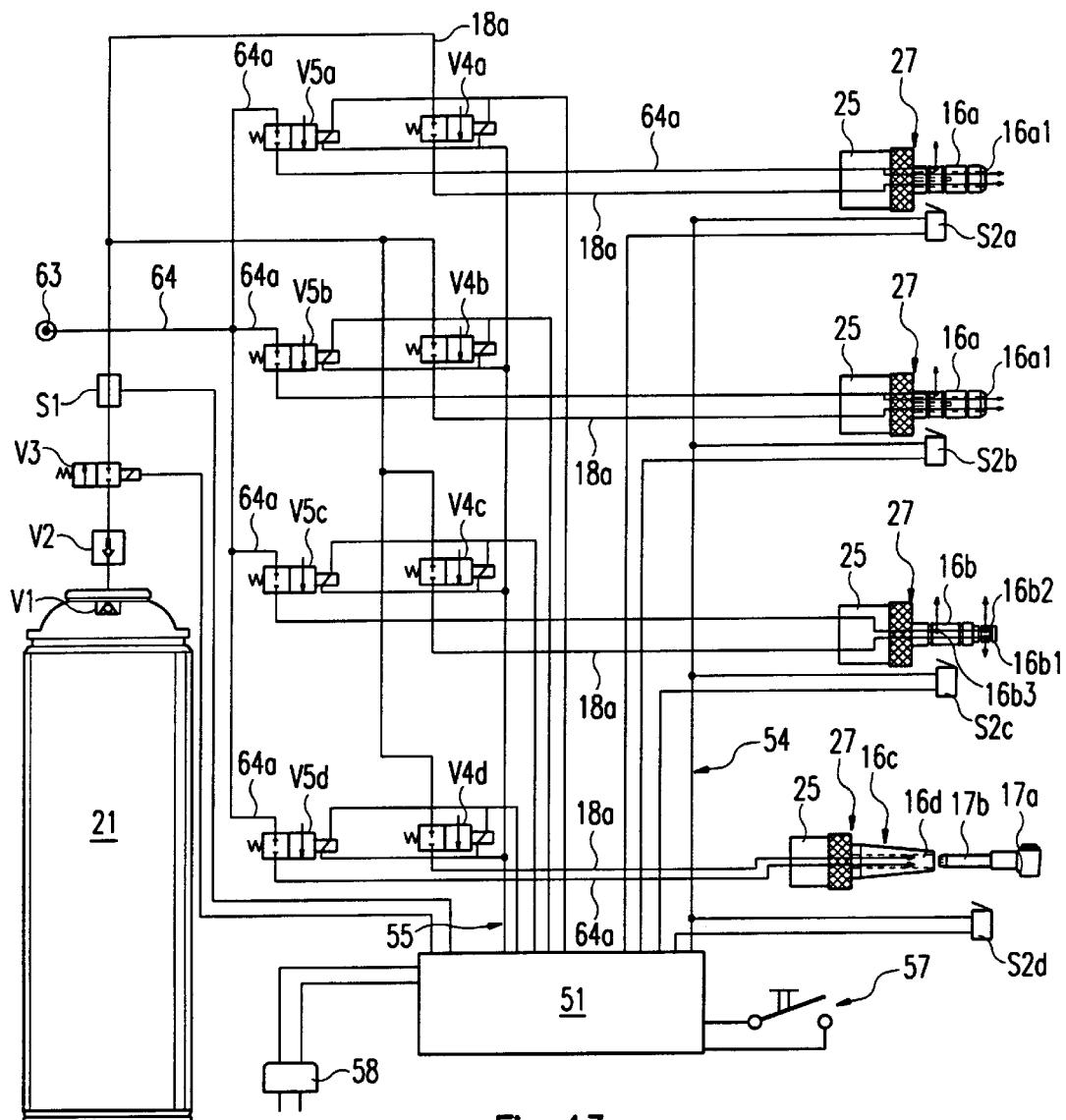
FIG. 13 a circuit diagram for a second exemplary embodiment of the device.

The exemplary embodiment of the maintenance apparatus 1 according to FIG. 13, in which the same or similar parts are provided with the same reference signs, has the following additional features. A compressed air source 63 and/or a compressed air line 64 is present which in the case of use is to be connected with a compressed air source 63. The compressed air line 64 branches into compressed air line branches 64a, in which in each case a fifth valve V5a to V5d is arranged, which is connected with the control apparatus 51 by means of a control line branch of the control lines 55 and is thus controllable and can be opened together with the valves V4a to V4d. The compressed air line branches 64a extend to the exit openings 16a1, 16b1 in the associated plug-in connection parts 16. With such a configuration, maintenance medium and compressed air are conveyed at the same time through the drive channels of the handpieces 17, whereby the compressed air not only promotes the cleaning effect but also finely divides the maintenance medium, prevents a collection a excessive maintenance medium, and thus improves the maintenance.

Figures 14, 15:
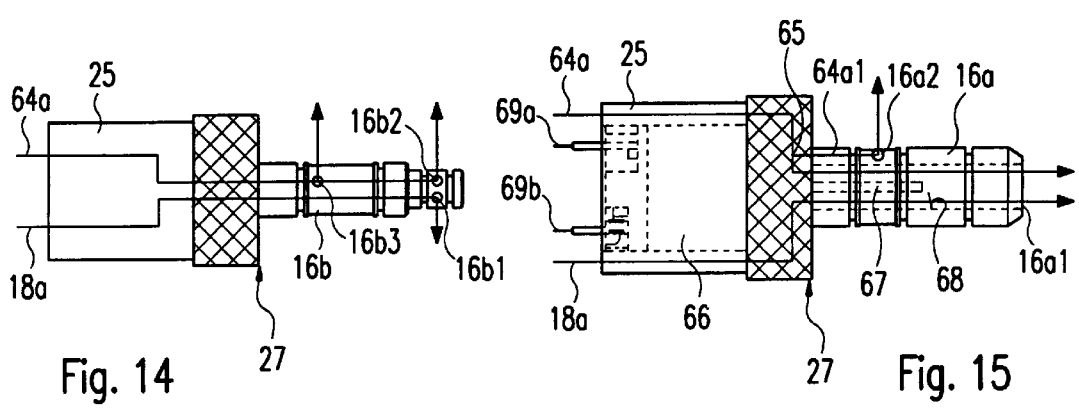
FIG. 14 a plug-in connection part for a handpiece, illustrated to an enlarged scale.
FIG. 15 a plug-in connection part, in a modified configuration.

As is in particular shown by the enlarged illustration according to FIG. 14 of the plug-in connection part 16b, the maintenance medium line branch 18a extends to its own exit opening 16b1 and the compressed air line branch 64a extends to a second exit opening 16b2 arranged in the same transverse plane, which second opening, in the case of a coupled turbine handpiece 17, likewise stands in connection with its drive channel. Further, the compressed air line branch 64a is connected with an exit opening 16b3, axially offset at the outer surface of the plug-in connection part 16b, which exit opening in the case of a plugged-in handpiece 17 stands in connection with its at least one media channel, so that in the maintenance procedure the compressed air blasts out and cleans the media channel. By means of the presence of two exit openings 16b1, 16b2, on the one hand for the maintenance medium and on the other hand for the compressed air, the danger is reduced that maintenance medium reaches the exit opening 16b3 and into the media channel.

In the case of the presence of a plug-in connection part 16a, as is shown to an enlarged scale in FIG. 15, the compressed air branch 64a is likewise connected with an axially offset opening 16a2 at the outer surface of the plug-in connection part 16a, which with plugged-in handpiece 17 is connected with at least one media channel of the handpiece 17, in order to blast through and clean the media channel in a maintenance procedure. In order to reduce the danger of a penetration of maintenance medium through the exit opening 16a2 also with the configuration of FIG. 15, a further compressed air line branch 64a1 branches off, at the branch 65, from the compressed air line branch 64a before—in the direction of flow—the exit opening 16a2, or also before the plug-in connection part 16a, which further compressed air line branch extends to the exit opening 16a2. Within the scope of the invention the control of the valves V5a to V5d may be such that before the supply of maintenance medium a pulse of compressed air is passed, which cleans the drive channel and if appropriate also the media channel, before maintenance medium is supplied. Further, within the scope of the invention it is possible to pass a compressed air pulse not simultaneously with a maintenance medium feed but time delayed after the flowing through of the drive channel with maintenance medium, through the respective associated valve by means of opening of the same, so that the compressed air pulse brings about a blasting out of the cleaned drive channel and thereby finely distributes the maintenance medium, blows out solid components of old maintenance medium and excessive maintenance medium, and thus likewise improves the maintenance. Simultaneously the at least medium one channel is also then blasted out.

Within the scope of the invention it is however also possible to send a first compressed air pulse through the at least one compressed air line branch 24a, simultaneously with the conveying of the maintenance medium, by control of the associated valve or valves V5a to V5d, and to send a second compressed air pulse after the conveying of the maintenance medium through the at least one branch line 64a, whereby the advantages which can be achieved with both above-described possibilities are also achieved.

The configuration according to FIG. 15 shows a further alternative configuration, which can be realized both with the configuration according to FIG. 12 and also with the configuration according to FIG. 13. with this variant, there is associated with the plug-in connection part or parts 16a, which serve for the coupling of a so-called motor handpiece, a rotation motor 16 having a rotation coupling extension 67. The rotation motor 66 is preferably integrated in or built into the carrier 25 or the rotation shaft or, with the presence of a connection device 27, the associated connection pin, whereby the rotation coupling extension 67 projects from behind into the hollow chamber 68 of the sleeve-like plug-in connection part 16a, so that the associated handpiece 17 stands in coupling connection with the rotation coupling extension 67 in the plugged-in condition of the coupling extension (not shown) extending from the fore into the hollow chamber 68, whereby this coupling connection upon plugging-in is self-actingly closed and by pulling off is self-actingly opened. The rotation motor 66 is connected with the control device 51 by means of electric lines 69a, 69b of an electrical current circuit and is controlled during the above-described maintenance medium through-flow and/or compressed air through-flow and put into rotation, whereby the drive parts arranged in the drive channel of the associated handpiece are likewise put into rotation and thereby both the cleaning effect and also the maintenance effect is or are improved due to the movement of the drive parts.

Figure 16:
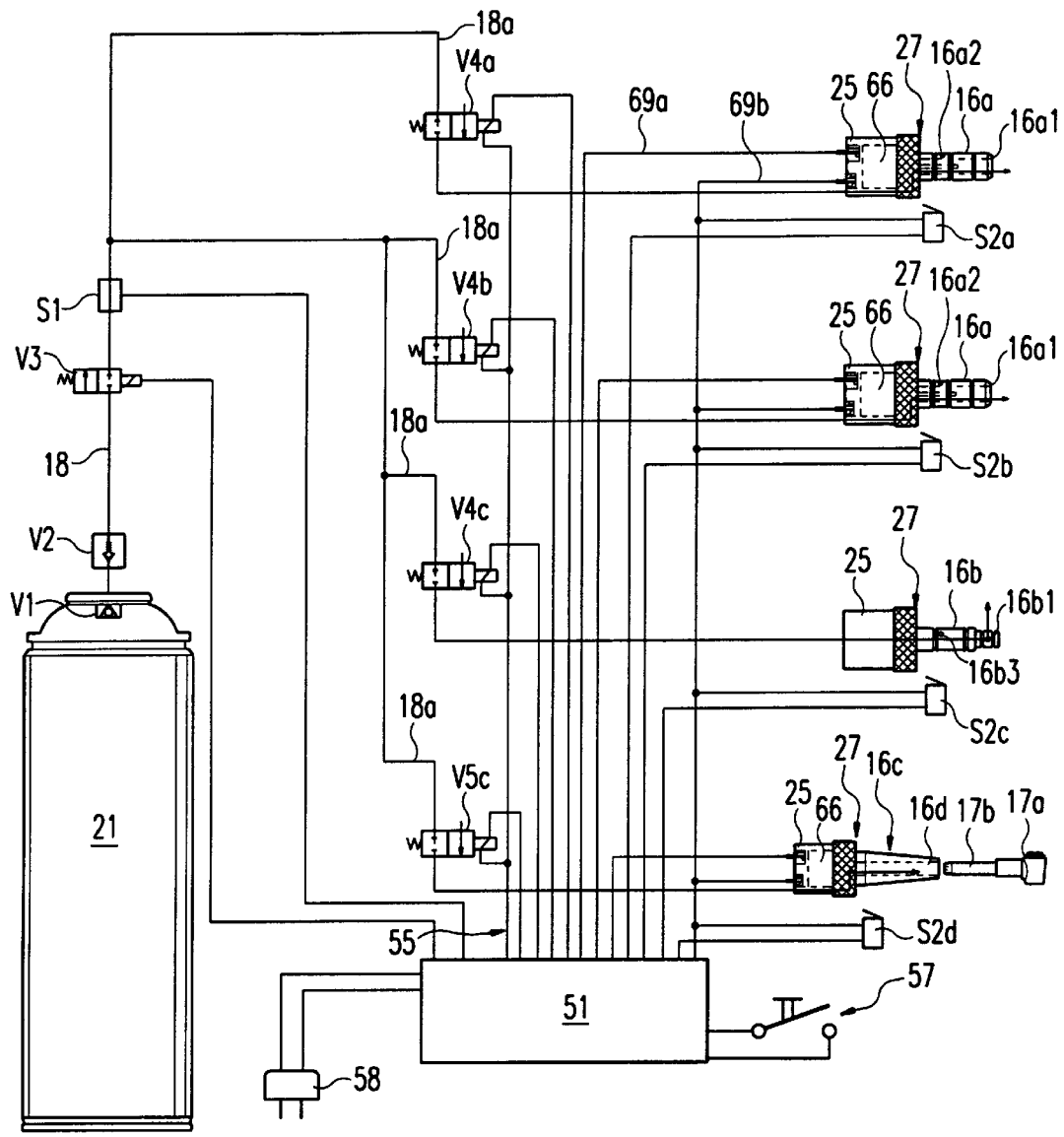
FIG. 16 a circuit diagram for a third exemplary embodiment of the device.
Figure 17:
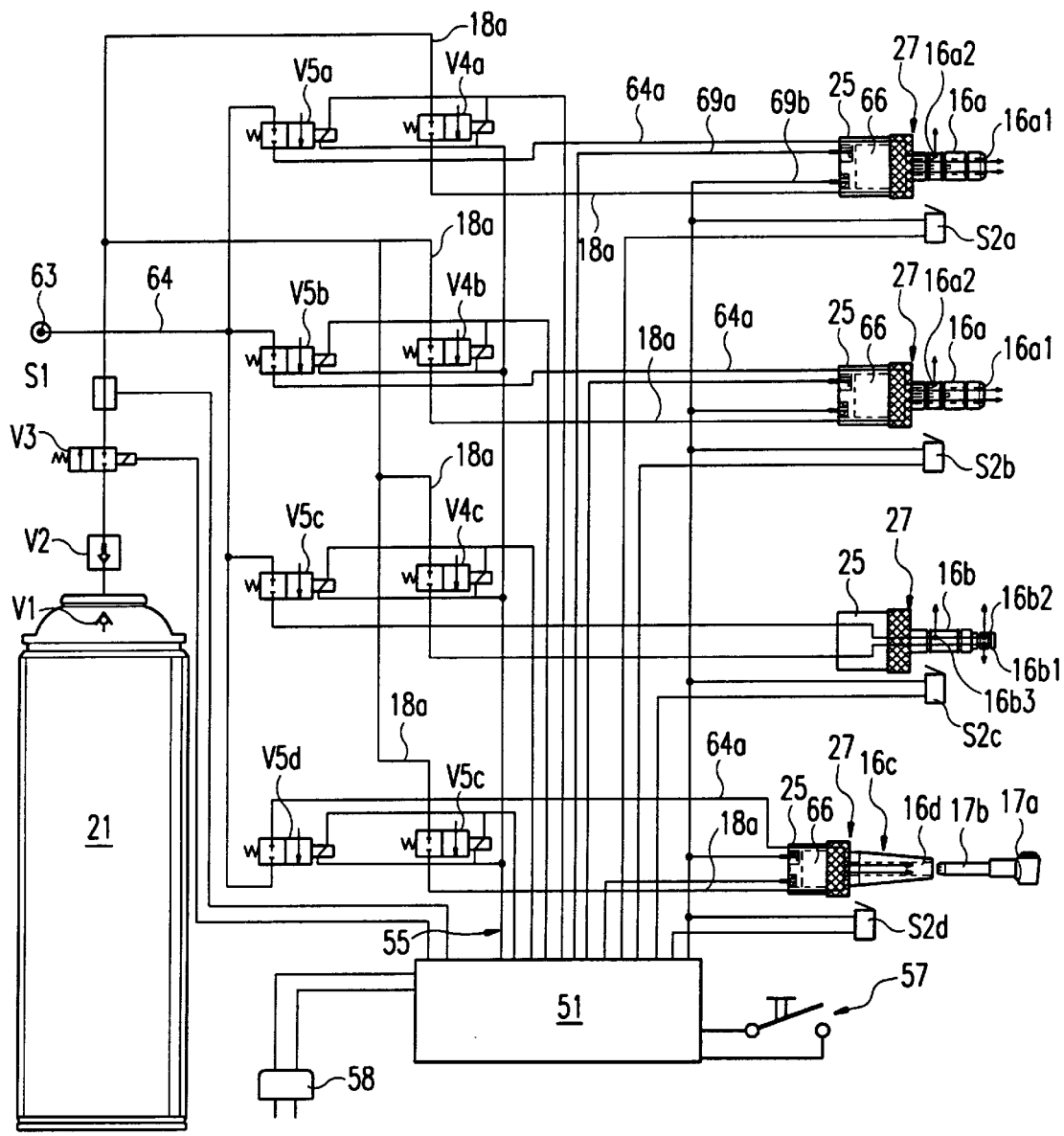
FIG. 17 a circuit diagram for a fourth exemplary embodiment of the device.

With the exemplary embodiment according to FIG. 16, which with regard to the passage of maintenance medium corresponds to the exemplary embodiment according to FIG. 12, in contrast to the exemplary embodiment according to FIG. 12 there is associated with the two plug-in connection parts 16a in each case a rotation motor 66 of the above-described kind. With the exemplary embodiment according to FIG. 16 there is, however, no compressed air supply present. Within the scope of the invention, this may however be present as is shown by the exemplary embodiment according to FIG. 15. With the exemplary embodiment according to FIG. 16 the sensors S2a to S2d are connected in parallel with the electrical line 69b, in which the rotation motors 66 are connected in series, by means of control or signal lines.

Within the scope of the present invention, one of the plug-in connection parts 16 can be formed as such a plug-in connection part 16c that is especially equipped to be connected with a so-called handpiece head 17a, so that also such a handpiece head 17a can be cleaned and/or maintained in the above-described manner. Such a handpiece head 17a is a known component produced by the applicants, and it has a handpiece head shaft 17b which can be plugged into a plug-in hole 16d of the plug-in connection part 16c, here formed as a sleeve, whereby the compressed air line branches 64a and maintenance medium line branches 18a may be configured in the manner of the configuration according to FIG. 15 and open out in the plug-in hole 16d, from where the maintenance medium and/or the compressed air is able to flow further in a drive channel axially running in the handpiece head shaft 17b. With this plug-in connection part 16c also, there can also be arranged a rotation motor 66 having a rotation coupling extension 67 in the above-described manner, in order to put into rotation a drive shaft train arranged in the drive channel of the handpiece head shaft 17b during the cleaning and/or maintenance. Such a plug-in connection part 16c can be provided in all present exemplary embodiments, such as is shown e.g. by FIG. 13.

Figure 18:
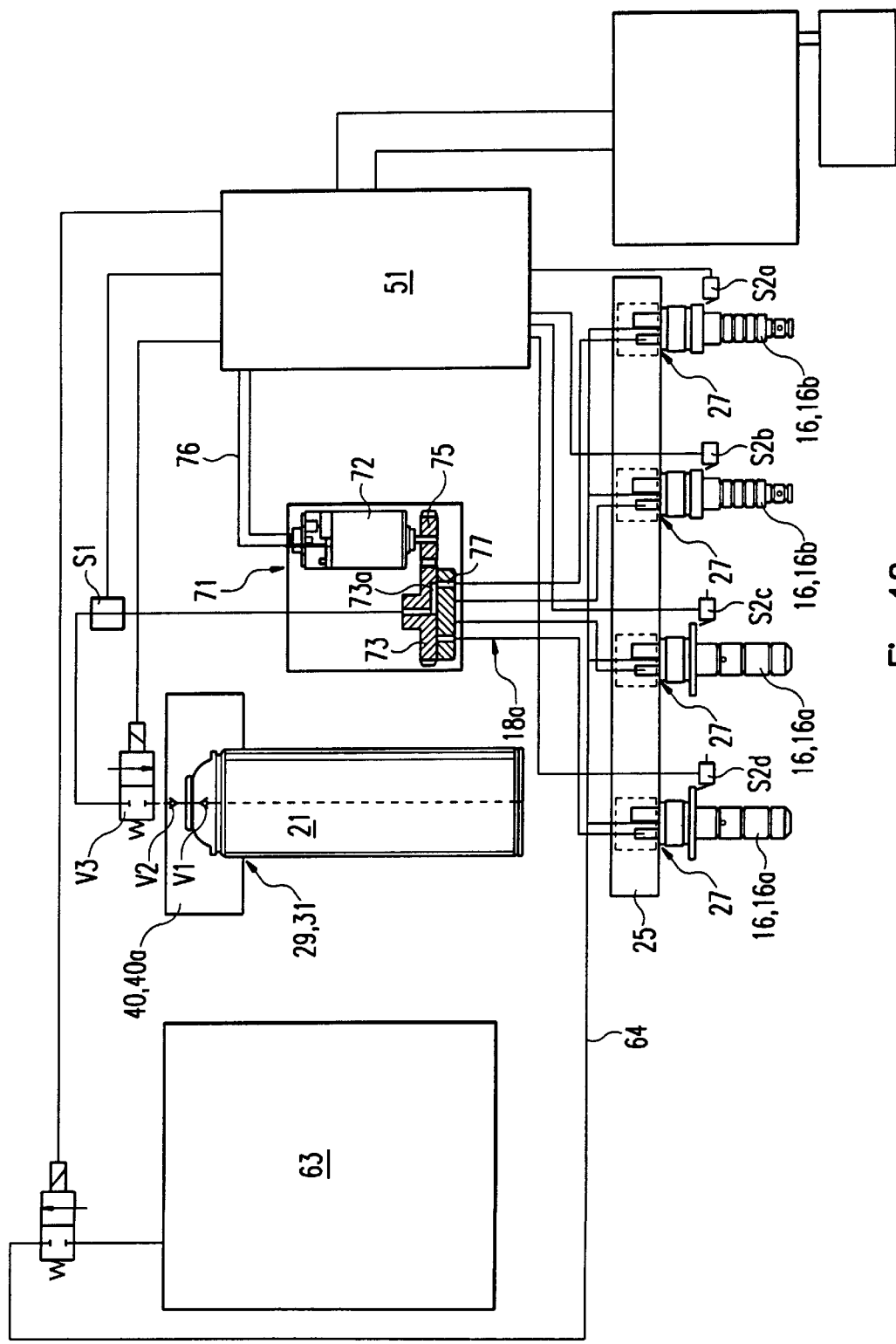
FIG. 18 a circuit diagram for a fifth embodiment of the device.

The exemplary embodiment according to FIG. 18, with which the same or similar parts are likewise provided with the same reference signs, corresponds largely to the exemplary embodiment according to FIG. 16, whereby however a different maintenance medium supply and maintenance medium quantity control is provided. With this configuration, instead of the distributor valves V4a to V4d, there is a distributor device 71 having a stepping motor 72, a distributor rotation disk 73, which is rotatably mounted and stands in rotation drive connection with the stepping motor 72, and a distributor disk 74 which bears flatly coaxially on the distributor rotation disk 73 and cooperates therewith in a distributor function. With the present exemplary embodiment, the stepping motor 72 stands in drive connection with the distributor rotation disk 73 by means of a toothed wheel 75, which engages with the distributor rotation disk 73, which is constituted as a toothed wheel. The stepping motor 72 is connected with the control device 51 by means of electrical lines 76 of a current circuit and thus controllable by means of the control device 51. The distributor disk 74 has through holes 77—of a number equal to the number of the plug-in connection parts 16 present— which e.g. may be arranged on a pitch circle. From valve V3 present, the supply line 18 extends preferably coaxially to the distributor rotation disk 73, which has an e.g. angle-shaped supply channel 73a, which so opens out that the preferably planar disk side towards the distributor disk 74 that in a respective determined rotational disposition it stands in connection with one of the through holes 77. Supply line branches 18a extend from the through holes 77 to the plug-in connection parts 16, with each of which a sensor S2a to S2d is associated, as has already been described above.

Also with this variant, the control device 51 recognizes on the basis of the signals of the sensors S2a to S2d which plug-in connection parts 16 are occupied with handpieces 17 or not. Correspondingly, in the maintenance procedure, the distributor rotation disk 73 is so rotated by means of the stepping motor that a flow passage between the supply line 18 and the respective associated supply line branch 18a is present. In this position of the distributor rotation disk 73 a dosing of the maintenance medium flowing to the associated plug-in connection part is effected in that the valve V3 is controlled by means of the control device 51 and opened for a certain time. The running of these individual maintenance procedures occurs automatically one after another, so that all occupied plug-in connection parts 16, including the handpieces 17 located there, are flowed through with maintenance medium. Otherwise, the function of the exemplary embodiment according to FIG. 18 corresponds to the already described function of the maintenance apparatus 1, whereby a compressed air supply 63 with compressed air line branches 64a and/or respective rotation motors 66 may be associated with the plug-in connection parts 16a in the above-described manner.

What is claimed is:

1. Maintenance apparatus for medical or dental handpieces, having a housing, which encloses a free maintenance chamber which is accessible by means of a door, having a plurality of connection parts in the maintenance chamber each for receiving the rearward end of a handpiece, having a supply line for a maintenance medium, which branches with supply line branches to the connection parts, which branches open out each at a mouth opening at the associated connection part, which stands in connection with a drive channel of the connected handpiece, having a supply system for supplying the maintenance medium to the connection parts and having a control device for control of the supply system, whereby a sensor is associated with each connection part, which sensor is activated by means of the handpiece connected with the associated connection part and emits a signal to the control device, and whereby the supply system supplies the maintenance medium only to the connection parts which are connected with a handpiece the supply system being constructed and arranged to supply the maintenance medium to the connection parts one after another.

2. Maintenance apparatus according to claim 1, wherein a spray can is provided as maintenance medium source, which is connected with the supply line.

3. Maintenance apparatus for medical or dental handpieces, having a housing, which encloses a free maintenance chamber which is accessible by means of a door, having a plurality of connection parts in the maintenance chamber each for receiving the rearward end of a handpiece, having a supply line for a maintenance medium, which branches with supply line branches to the connection parts, which branches open out each at a mouth opening at the associated connection part, which stands in connection with a drive channel of the connected handpiece, having a supply system for supplying the maintenance medium to the connection parts and having a control device for control of the supply system, whereby a sensor is associated with each connection part, which sensor is activated by means of the handpiece connected with the associated connection part and emits a signal to the control device, and whereby the supply system supplies the maintenance medium only to the connection parts which are connected with a handpiece, wherein the supply system is constructed and arranged to supply the maintenance medium to the mouth openings of a number of connection parts which is reduced with regard to the number of connection parts present, and in that a spray can is provided as maintenance medium source, which is connected with the supply line.

4. Maintenance apparatus according to claim 1 or 3, wherein the sensor is arranged on a non-moveable interior wall of the maintenance chamber.

5. Maintenance apparatus according to claim 1 or 3, wherein the handpiece is constructed and arranged to move into connection disposition and contact with the sensor and to further move beyond this contact without damaging or overloading the sensor.

6. Maintenance apparatus according to claim 1 or 3, wherein the connection parts are adapted to handpieces which differ from each other in at least one of the group consisting of shape, size and function.

7. Maintenance apparatus according to claim 1 or 3, wherein the supply system includes a valve arranged in the common supply line and respective valves in the supply line branches.

8. Maintenance apparatus according to claim 1 or 3, wherein the supply system is configured to be connected to a compressed air source for the purpose of issuing a compressed air flow to one of the supply line and the supply line branches in timed relationship with the supply of maintenance medium.

9. Maintenance apparatus according to claim 8, wherein a supply line for compressed air extends with supply line branches in each case to the mouth openings of at least one of the connection parts.

10. Maintenance apparatus according to claim 8, wherein the supply line for compressed air extends with supply line branches to at least one connection part and in each case opens at a second mouth opening which stands in connection with the at least one media channel of the handpiece, in the connected disposition of the handpiece in the associated connection part.

11. Maintenance apparatus according to claim 10, wherein in each case a common supply line branch for compressed air branches to the first and the second mouth opening, whereby the branch is arranged, in the flow direction, before the mouth openings.

12. Maintenance apparatus according to claim 1 or 3, wherein the supply system includes a distributor element connecting the common supply line with a supply line branch.

* * * * *